United States Patent
Rather et al.

(10) Patent No.: US 11,780,868 B1
(45) Date of Patent: Oct. 10, 2023

(54) HOMOLEPTIC METAL COORDINATION COMPLEXES AS ANTIFUNGAL AGENTS

(71) Applicant: King Abdulaziz University, Jeddah (SA)

(72) Inventors: Irfan Ahmad Rather, Jeddah (SA); Majid Rasool Kamli, Jeddah (SA); Khalid Rehman Hakeem, Jeddah (SA); Ahmad Firoz, Jeddah (SA); Jamal S. M. Sabir, Jeddah (SA); Mohmmad Younus Wani, Jeddah (SA); Yong Ha Park, Gyeongsanbuk-do (KR); Yan Yan Hor, Gyeongsanbuk-do (KR)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 18/141,200

(22) Filed: Apr. 28, 2023

(51) Int. Cl.
| | |
|---|---|
| C07F 15/06 | (2006.01) |
| A61P 31/10 | (2006.01) |
| C07F 15/04 | (2006.01) |
| A01P 3/00 | (2006.01) |
| A01N 59/16 | (2006.01) |
| A01N 59/20 | (2006.01) |
| A01N 55/02 | (2006.01) |
| C07C 209/60 | (2006.01) |

(52) U.S. Cl.
CPC ............... *C07F 15/06* (2013.01); *A01N 55/02* (2013.01); *A01N 59/16* (2013.01); *A01N 59/20* (2013.01); *A01P 3/00* (2021.08); *A61P 31/10* (2018.01); *C07F 15/045* (2013.01); *C07F 15/065* (2013.01); *C07C 209/60* (2013.01)

(58) Field of Classification Search
CPC ......... A01N 55/02; A01N 59/00; A61P 31/00; A01P 3/00; C07F 15/00; C07C 206/60
See application file for complete search history.

(56) References Cited

U.S. PATENT DOCUMENTS

| | | | | |
|---|---|---|---|---|
| 3,652,770 A | * | 3/1972 | Rohr et al. | ............ C07C 255/00 504/183 |
| 3,721,741 A | * | 3/1973 | Rohr et al. | ........... A61K 31/135 514/514 |

OTHER PUBLICATIONS

Creaven et al., "Anticancer and antifungal activity of copper(II) complexes of quinolin-2(1H)-one-derived Schiff bases," Inorganica Chimica Acta 363, 4048-58. (Year: 2010).*

Dar et al., "Heteroleptic transition metal complexes of Schiff-base-derived ligands exert their antifungal activity by disrupting membrane integrity," Applied Organometallic Chemistry 33, e5128. (Year: 2019).*

Shi et al., Synthesis, characterization and antimicrobial property in vitro of supramolecular coordination polymers bearing brominated Schiff base ligand, Journal of Inorganic Biochemistry 236, 111939. (Year: 2022).*

* cited by examiner

*Primary Examiner* — Theodore R. Howell
(74) *Attorney, Agent, or Firm* — WCF IP

(57) ABSTRACT

Provided herein are homoleptic metal coordination complexes that induce cellular apoptosis and cell cycle arrest in G0/G1 phase in fungus, such as *Candida* spp. Also disclosed are methods of inhibiting fungal growth and methods of treating fungal infections using the disclosed compounds. The disclosed compounds exhibit anti-*Candida* activity against fluconazole resistant and sensitive strains of *C. albicans* at low concentrations.

12 Claims, 9 Drawing Sheets

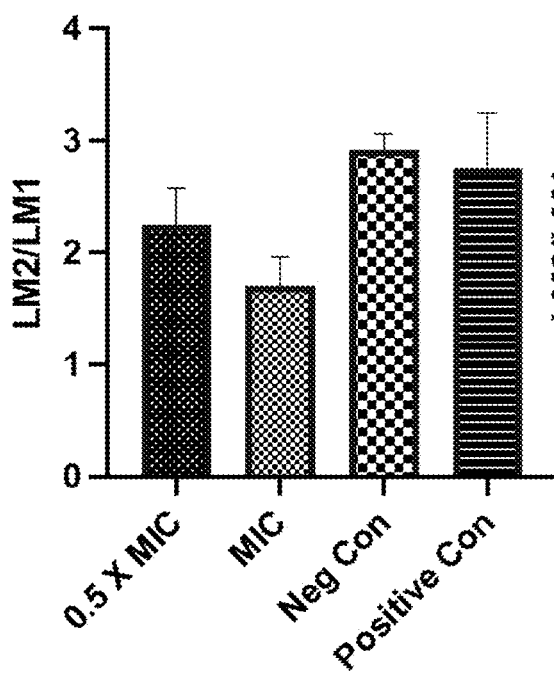 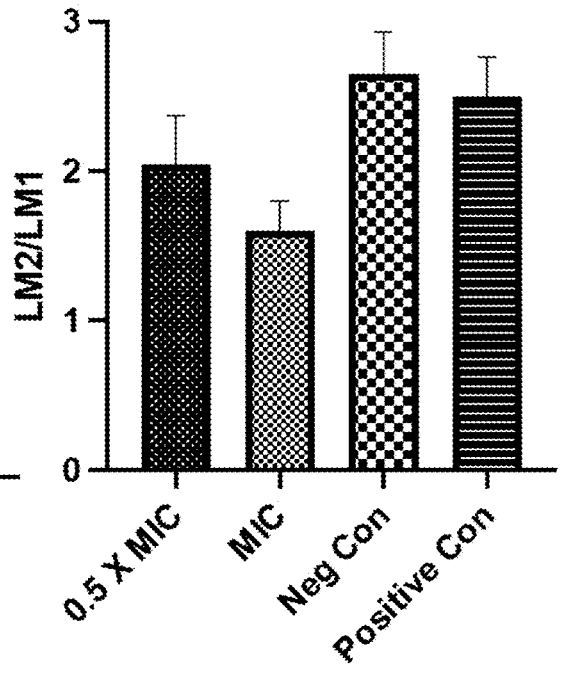
FIG. 5A  FIG. 5B
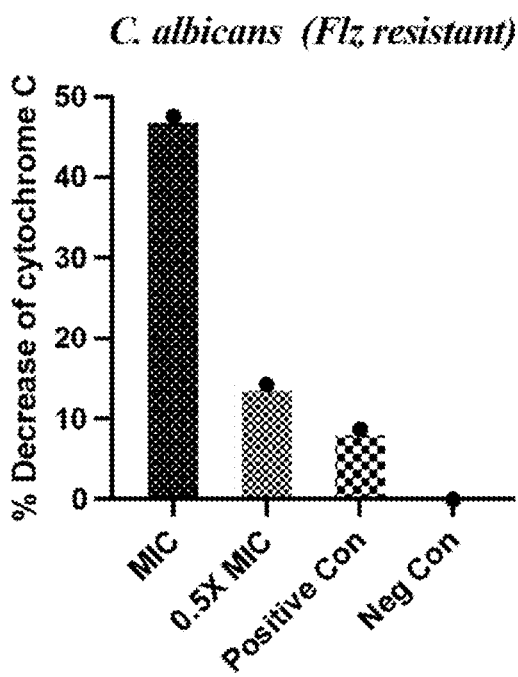 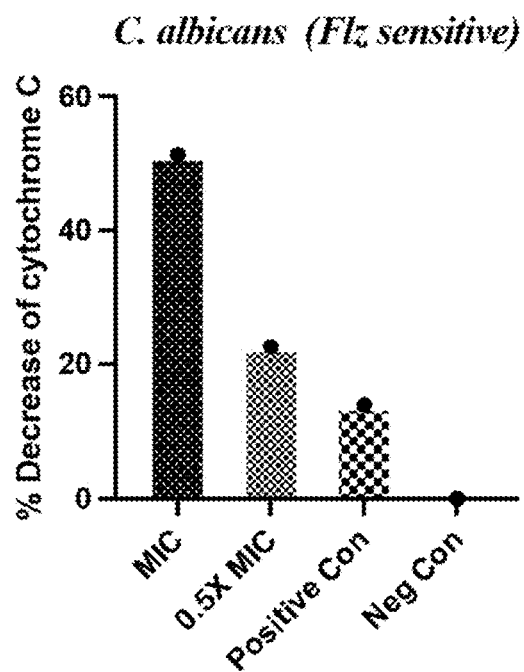
FIG. 6A  FIG. 6B

FIG. 7A  FIG. 7B  FIG. 7C  FIG. 7D
   
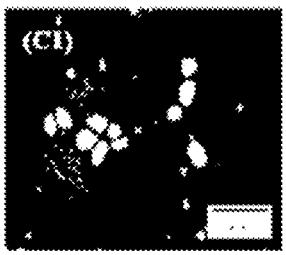 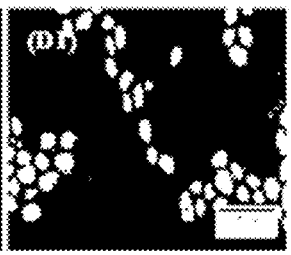  
*C. albicans* 5112 (Flz resistant)  *C. albicans* 4251 (Flz susceptible)
FIG. 7E  FIG. 7F  FIG. 7G  FIG. 7H

HOMOLEPTIC METAL COORDINATION COMPLEXES AS ANTIFUNGAL AGENTS

FIELD OF THE INVENTION

The disclosure provides antifungal agents that induce cellular apoptosis and cell cycle arrest in the G0/G1 phase of drug-resistant fungi. In particular, these molecules control and combat infections caused by fluconazole-resistant *C. albicans* in immunocompromised patients.

BACKGROUND

Fluconazole is one of the most important members of the family of azole antifungals as it is orally active and has low toxicity, but its extensive use has resulted in emergence of fluconazole-resistant fungal strains. This has made it necessary to develop analogues of fluconazole effective against resistant strains, and many new compounds have been reported. However, issues like toxicity, solubility, cost, broad spectrum of activity, etc. have led to the need to develop superior antifungal agents. The structure-activity relationship studies in the case of fluconazole have shown that the presence of one triazole ring, halogenated phenyl ring and tertiary alcoholic oxygen functionality is necessary for activity.

Some articles describing synthesis and antifungal activity of fluconazole analogues include: Chemistry and Biodiversity 4, 1472 (2007); Bioorg. Med. Chem. Lett. 17(13), 3686 (2007); Bioorg. Med. Chem. 16, 7055 (2008); Bioorg. Med. Chem. Lett. 18, 3261 (2008); Bioorg. Med. Chem. Lett. 18, 6538 (2008); Bioorg. Med. Chem. Lett. 19, 2013 (2009); and Bioorg. Med. Chem. Lett. 20, 722 (2010).

Fungal infections are a huge menace for immunocompromised individuals on a global scale. *Candida albicans* is said to be the third most common fungal pathogen in United States hospitals. Based on epidemiological studies, *C. albicans* is responsible for around 25% of superficial fungal infections globally. Being a commensal and opportunistic pathogen, *C. albicans* can colonize in oral, vaginal, gastrointestinal, and cutaneous surfaces of the host. Hence, candidiasis is a leading cause of nosocomial infection, surpassing most bacterial infections.

Unlike most bacterial diseases, fungal diseases are difficult to treat. Additionally, systemic candidiasis is linked with a high rate of mortality in immunocompromised individuals. In the past few years, the escalating use of drugs for the treatment of *Candida* infections ranging from superficial to invasive has resulted in the emergence of drug-resistant strains of *C. albicans*. Therefore, the development of a potential anti-*Candida* agent with lesser toxicities has become a high priority in the field.

Moreover, individuals suffering from conditions such as HIV/AIDS, organ transplantation, and chemotherapy are expected to rise over the next ten years and these patients are susceptible to *Candida* infections with serious side effects. Thus, the requirement for a novel anti-*Candida* agent with targeted action is increasing.

*C. albicans* are capable enough to perform morphological switching between the yeast and the hyphal form and therefore they have better dispersal as well as invasive properties. The hyphal form penetrates the host cell and helps acquire nutrients for the growing yeast cells thus damaging host tissues or organs.

Despite increasing numbers of health-compromised people, who are prone to life-threatening fungal infection, only four classes of antifungal drugs are approved by the USFDA for treating infections caused by *Candida* species. These drugs include polyenes, azoles, echinocandins, and flucytosine. Although current medications could prevent infections, the problem arises when the microbes develop resistance to different defense mechanisms.

The polyene class of antifungals are associated with dose-related toxicity, mainly nephrotoxicity, however, the discovery of lipid formulations has lowered the risk factors. Further, of more importance, increasing drug resistance is an unavoidable problem. The reduction of fluconazole susceptibility in *C. albicans* strains is becoming a challenge for HIV patients, although second—generation antifungals (triazole agents and echinocandins) have addressed some issues. However, treatment failures and the advent of resistance against echinocandin antifungal agents have been reported and therefore, the mortality rates for candidemia remain high. This situation thus emphasizes the pressing need for more effective and less toxic antifungal agents against *C. albicans* infection.

With the first therapeutic metallodrug "salvarsan" and the serendipitously discovered "cisplatin" (Platinol), it began to be possible to fight dreadful diseases through a systematic search of metallodrugs that kill the microbes without causing any damage to the host. Many, if not most, metallopharmaceuticals are prodrugs that undergo redox changes and/or ligand exchange reactions in vivo to generate the active species. Hence, metallodrugs may be a substitute for conventional organic drugs, because complexation may lead to the synergistic effect of both metal ions and ligands. In addition, metal complexes trigger the inactivation of enzymes essential for the survival of cells, resulting in several morphological changes, agglutination and lysis and are thus fatal for pathogenic microorganisms. Development of new metal-based drugs that may be used to fight resistant fungal infections that are otherwise difficult to treat using conventional antifungal therapies is needed.

SUMMARY

In light of the disadvantages of the prior art, the following summary is provided to facilitate an understanding of some of the innovative features unique to the present invention and is not intended to be a full description. A full appreciation of the various aspects of the invention can be gained by taking the entire specifications, claims, drawings, and abstract as a whole.

Provided herein are antifungal agents that induce cellular apoptosis and cell cycle arrest in the G0/G1 phase of fungi, such as drug-resistant *Candida* spp. In particular, these molecules control and combat infections caused by fluconazole-resistant *C. albicans* in immunocompromised patients.

One aspect of the disclosure provides a metal coordination complex, having the following formula:

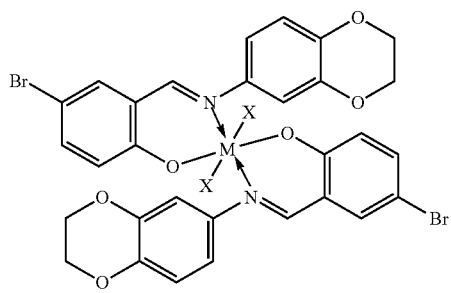

wherein
M is a transition metal; and
X is present or absent, and when present, is $H_2O$.

In some embodiments, M is selected from the group consisting of cobalt, nickel, copper, and zinc.

Another aspect of the disclosure provides a pharmaceutical composition comprising a metal coordination complex as described herein and a pharmaceutically acceptable carrier.

Another aspect of the disclosure provides a method of inhibiting growth of a fungus comprising contacting the fungus with an effective amount of a metal coordination complex as described herein. In some embodiments, the fungus is *Candida* spp, such as *Candida albicans*. The fungus may be resistant or susceptible to azole antifungal agents, such as fluconazole.

Another aspect of the disclosure provides a method of treating a fungal infection in a subject in need thereof comprising administering to the subject a therapeutically effective amount of a metal coordination complex as described herein. In some embodiments, the fungus is *Candida* spp, such as *Candida albicans*. The fungus may be resistant or susceptible to azole antifungal agents, such as fluconazole.

Another aspect of the disclosure provides a method for synthesizing a ligand having the formula (E)-4-bromo-2-{[(2,3-dihydrobenzo[b][1,4]dioxin-6-yl)imino]methyl}phenol, comprising reacting 2,3-dihydrobenzo[b][1,4]dioxin-6-amine with 5-bromo-2-hydroxybenzaldehyde under conditions suitable for forming the ligand.

Additional features and advantages of the present invention will be set forth in the description of disclosure that follows, and in part, will be apparent from the description of may be learned by practice of the disclosure. The disclosure will be realized and attained by the compositions and methods particularly pointed out in the written description and claims hereof.

BRIEF DESCRIPTION OF THE DRAWINGS

FIGS. 5A-B. Mitochondrial depolarization effect of C1 in (A) *C. albicans* 5112 (Flz resistant) cells and (B) *C. albicans* 4251 (Flz susceptible) cells. The graph represents the fluorescence ratio (Y mean/X mean). Y mean represents JC-10 aggregates and X mean represents JC-10 monomers.

FIG. 6A-B. Effect of C1 on the activity of cytochrome c oxidase in (A) *C. albicans* 5112 (Flz resistant) cells and (B) *C. albicans* 4251 (Flz susceptible) cells. *C. albicans* cells were exposed to various concentrations of C1 (0.5×MIC and 1×MIC).

FIGS. 7A-H. Fluorescence images of *C. albicans* cells after exposure to 0.5×MIC and 1×MIC of C1. Untreated cells (A, C); cells exposed to hydrogen peroxide (B, D); cells exposed to 0.5×MIC (E, G); cells exposed to 1×MIC (F, H).

DETAILED DESCRIPTION

Figure 1:
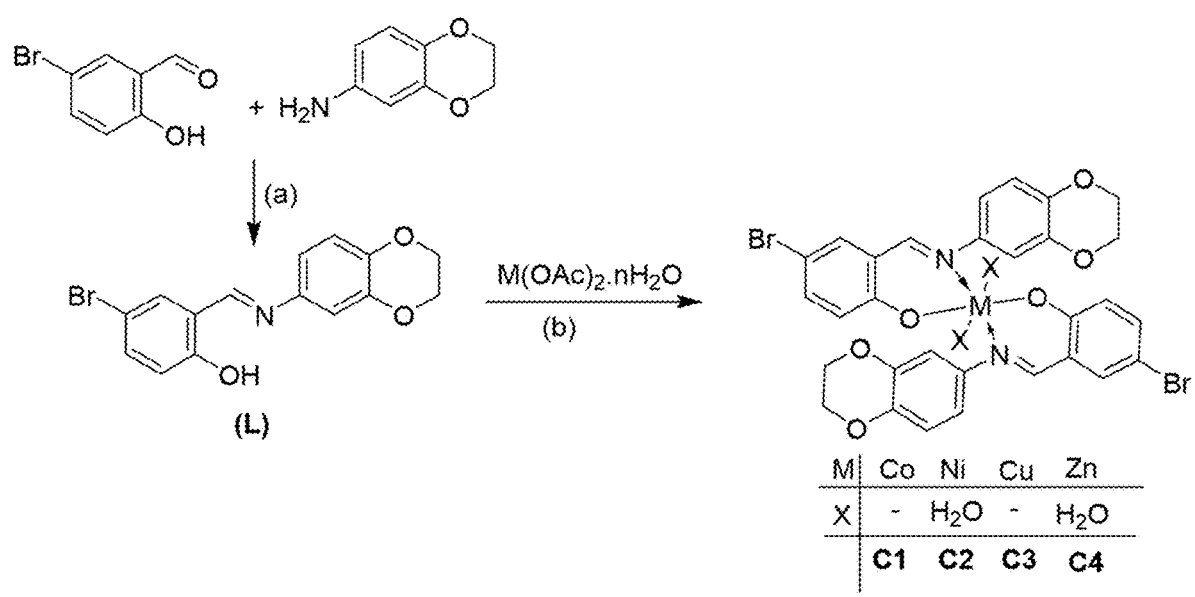
FIG. 1. Schematic of the synthesis of the ligand (L) and homoleptic metal complexes C1-C4. Reaction conditions: (a) Ethanol, reflux (b) 1:1 mixture of methanol and dichloromethane, room temperature.

Detailed descriptions of the preferred embodiments are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The preferred embodiments of the present disclosure are directed toward molecules that have antifungal activity against fluconazole (Flz)-resistant and susceptible strains of *C. albicans*. As demonstrated in the Example, the minimum inhibitory concentration (MIC) value of an exemplary molecule ranged from 1.22-4.88 µg/mL for Flz susceptible strains whereas, 9.76-19.53 µg/mL was recorded for Flz resistant strains. The minimum fungicidal concentration (MFC) values were 2.44-9.76 µg/mL and 19.53-78.12 µg/mL for Flz susceptible strains and resistant strains respectively. The most active compound at its sub-MIC dosage effectively induced cell-mediated apoptosis and was capable of arresting the cell cycle in G0/G1 phase. Additionally, a negligible amount of haemolytic activity was found associated with this compound.

Embodiments of the disclosure provide a metal coordination complex, having the following formula:

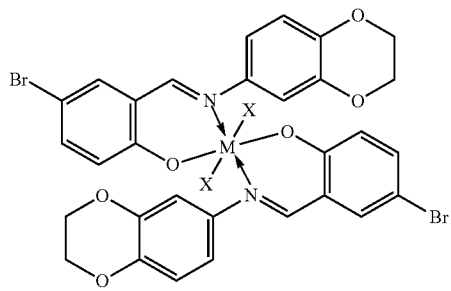

wherein
M is a transition metal; and
X is present or absent, and when present, is $H_2O$.

The homoleptic coordination complex comprises two (E)-4-bromo-2-{[(2,3-dihydrobenzo[b][1,4]dioxin-6-yl)imino]methyl}phenol ligands chelated to a transition metal ion. The ligand behaves as a NO bidentate coordinating ligand, coordinating through its iminic-N and phenolate-O atoms.

In some embodiments, the transition metal is a group 3, group 4, group 5, group 6, group 7, group 8, group 9, group 10, group 11, or group 12 transition metal. In some embodiments, the transition metal is selected from the group consisting of cobalt, nickel, copper, and zinc.

In some embodiments, cobalt is the central metal ion and the complex displays a tetrahedral geometry. In some embodiments, copper is the central metal ion and the complex displays a square planar geometry. In some embodiments, nickel or zinc are the central metal ion and the complex displays octahedral geometry. The geometry of the complex can be altered by changing the reaction conditions and metal salts (Platinum or Palladium) used in the synthesis of the complex.

Further embodiments provide a pharmaceutical composition comprising a metal coordination complex as described herein and a pharmaceutically acceptable carrier. "Pharmaceutically" or "pharmaceutically acceptable" refer to molecular entities and compositions that do not produce an adverse, allergic, or other untoward reaction when administered to a mammal, especially a human, as appropriate. A pharmaceutically acceptable carrier or excipient refers to a non-toxic solid, semi-solid or liquid filler, diluent, encapsulating material or formulation auxiliary of any type.

Suitable pharmaceutically acceptable carriers include but are not limited to water, salt solutions, alcohols, gum arabic, vegetable oils, benzyl alcohols, polyethylene glycols, gelate, carbohydrates such as lactose, amylose or starch, magnesium stearate talc, silicic acid, viscous paraffin, perfume oil, fatty acid monoglycerides and diglycerides, pentaerythritol fatty acid esters, hydroxymethylcellulose, polyvinylpyrrolidone, etc. The pharmaceutical preparations can be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. Other suitable excipients include, for example an inert diluent such as lactose; granulating and disintegrating agents such as cornstarch; binding agents such as starch; and lubricating agents such as magnesium stearate.

In another embodiment of the present disclosure, the excipient in the composition is selected from the group consisting of additive, solvent, oil, emulsifier, surfactant, stabilizer, cooling agent, preservative, antioxidant, gelling agent, moisturizing agent, emollient, penetration enhancer, colorant, fragrance, pH modifiers, conditioning agent, pearlizing agents, skin barrier repair agents, and combinations thereof.

The composition may contain any such additional ingredients so as to provide the composition in a form suitable for administration. The final amount of compound in the formulations may vary. However, in general, the amount in the formulations will be from about 1% to about 99%.

In some embodiments, the composition is an oily solution or suspension. In some embodiments, the formulation is in a solid dosage form, such as a form selected from the group consisting of a tablet, dragee, capsule, caplet and gelcap.

In some embodiments, the composition is employed for the purpose of topical and/or local administration in the form of oils, creams, lotions, serums, gels, ointments, foams, sprays, aerosols, coating on implants, silicon tubes, catheters, sutures and the like.

In some embodiments, the composition comprises one or more additional antifungal agents. Suitable antifungal agents include, but are not limited to, allylamines, benzylamines, azoles, polyenes, echinocandins, N-hydroxy pyridone, N-hydroxy pyrithione, tavaborole, flucytosine, griseofulvin, hinokitol and combinations thereof. In some embodiments, the N-hydroxy pyridone is piroctone olamine, ciclopirox olamine or a combination thereof; the N-hydroxy pyrithione is zinc pyrithione or any respective bivalent metal coordinating complexes or combinations thereof; allylamines are selected from the group consisting of terbinafine, amorolfine, naftifine and combinations thereof; the benzylamine is butenafine; the azoles are imidazoles, triazoles or thiazoles selected from the group consisting of ketoconazole, climbazole, miconazole nitrate, fluconazole, econazole, saperconazole, oxiconazole, clotrimazole, bifonazole, butoconazole, fenticonazole, isoconazole, omoconazole, sertaconazole, sulconazole, tioconazole, luliconazole, chlormidazole, croconazole, eberconazole, omoconazole, isoconazole, neticonazole, albaconazole, efinaconazole, fosfluconazole, epoxiconazole, fluconazole, isavuconazole, itraconazole, posaconazole, propiconazole, ravuconazole, terconazole, voriconazole, hexaconazole, abafungin and combinations thereof; the polyenes are selected from the group consisting of amphotericin B, natamycin, nystatin and combinations thereof; and the echinocandins are selected from the group consisting of caspofungin, anidulafungin, micafungin and combinations thereof.

Embodiments of the present disclosure further provide methods of inhibiting growth of a fungus comprising contacting the fungus with an effective amount of a metal coordination complex as described herein. In some embodiments, the method is for treating a fungal infection in a subject in need thereof or managing fungal growth, comprising administering the metal coordination complex or pharmaceutical composition thereof described herein to the subject.

In an embodiment of the present disclosure, the method of treating or managing comprises inhibiting the fungal growth, reducing the fungal growth, eliminating the fungus, curing drug resistant fungal infections, treatment of fungal infections in clinical non-responders and patients with barrier defects, or any combination thereof.

In another embodiment of the present disclosure, the treatment described herein includes medical treatment, cosmetic treatment, or a combination thereof.

The methods and uses described herein may further include treating a subject in need thereof, comprising the steps of administering the complex or composition in an oral delivery vehicle, food product, nutritional supplement, dietary supplement, or functional food comprising the formulation to the subject. In some embodiments, the administration is oral, topical, parenteral, enteral, transdermal, intradermal, intraocular, intravitreal, sublingual, or intravaginal, and may preferably comprise an effective amount of the complex or composition.

In some embodiments, the composition is administered concomitantly or sequentially with one or more additional antifungal agents as described herein.

A patient or subject to be treated by any of the compositions or methods of the present disclosure can mean either a human or a non-human animal including, but not limited to dogs, horses, cats, rabbits, gerbils, hamsters, rodents, birds, aquatic mammals, cattle, pigs, camelids, and other zoological animals.

In some embodiments, the fungal infection or fungal growth is caused by fungi selected from the group consisting of *Candida* species, *Malassezia* species, *Trichophyton* species, *Microsporum* species, *Epidermophyton* species, *Aspergillus* species, *Cryptococcus* species and combinations thereof.

In another embodiment of the present disclosure, the fungal infection or fungal growth is caused by *Candida* spp. selected from the group consisting of *C. albicans, C. glabrata, C. guilliermondii, C. krusei, C. lusitaniae, C. parapsilosis, C. tropicalis, C. colliculosa, C. dubliniensis, C. famata, C. haemulonii, C. inconspicua, C. intermedia, C. kefyr, C. lipolytica, C. metapsilosis, C. norvegensis, C. orthopsilosis, C. pelliculosa, C. pulcherrima, C. nrugose. C. utilis, C. viswanathii,* and *C. zeylanoides; Malassezia* spp.

selected from the group consisting of *M. furfur*, *M. pachydermatis*, *M. globosa*, *M. restricta*, *M. sloofiae*, *M. sympodialis*, *M. nana*, *M. yamatoensis*, *M. dermatis*, *M. obtusa*, *M. japonica*, *M. caprae*, *M. cuniculi*, *M. equine*, and *M. arunalokei*; *Trichophyton* spp. selected from the group consisting of *T. rubrum*, *T. mentagrophyte*, *T. interdigitale*, *T. tonsurans*, *T. schoenleinii*, *T. violaceum*, *T. abissinicum*, *T. balcaneum*, *T. circonvolutum*, *T. concentricum*, *T. eboreum*, *T. errinacei*, *T. fischeri*, *T. fluviomuniense*, *T. glabrum*, *T. gourvilii*, *T. kanei*, *T. kuryangei*, *T. megninii*, *T. pedis*, *T. proliferans*, *T. raubitschekii*, *T. redellii*, *T. rodhainii*, *T. simii*, *T. soudanense*, *T. thuringiense*, *T. verrucosum*, *T. violaceum* and *Trichophyton yaoundei*; *Microsporum* spp. selected from the group consisting of *M. audouinii*, *M. canis*, *M. amazonicum*, *M. boullardii*, *M. cookie*, *M, distortum*, *M. duboisii*, *M equinum*, *M. ferrugineum*, *M. fulvum*, *M. gallinae*, *M. gypseum*, *M. langeronii*, *M. nanum*, *M. persicolor*, *M. praecox*, *M. ripariae* and *M. rivalieri*; *Epidermaphyton* spp such as *E. floccosum*; and other non-dermatophytes including but not limited to *Aspergillus* spp. selected from the group consisting of *A. fumigates*, *A. flavus*, *A. nidulans*, *A. terreus*, *A. lentulus*, *A. niger*, *A. alliaceus*, *A. arvii*, *A. brevipes*, *A. calidoustus*, *A. conjunctus*, *A. deflectus*, *A. duricaulis*, *A. emericella*, *A. fischerian*, *A. fumigatiaffinis*, *A. fumisvnnematus*, *A. granulosus*, *A. novofumigatus*, *A. panamensis*, *A. quadrilineatus*, *A. udagawae*, *A. unilateralis* and *A. ustus*; and *Cryptococcus* spp. selected from the group consisting of *C. neoformans*, *C. gattii*, *C. albidus*, *C. bacillisporus*, *C. decagatti*, *C. deuterogatti*, *C. laurentii*, *C. tetragatti* and *C. uniguttulatus*; or any combination of fungi thereof.

In some embodiments, the fungus is resistant or susceptible to an anti-fungal agent as described herein. Without wishing to be bound by a theory, the compositions described herein are particularly useful for treatment of fungal infections which are resistant to one or more conventional drugs used for treatment of fungal infections. For example, the compositions of the invention are particularly useful for treatment of fungal infections which are resistant to azoles (e.g. fluconazole), allylamines, and benzylamines.

As used herein, the terms "manage", "managing", "management", "treat", "treating" or "treatment" of fungus growth or fungus infection refers to both medical or non-medical indications. In one aspect, these terms cover one or more aspects including but not limiting to preventing or reducing growth of fungi, inhibiting further growth of fungi, eliminating the grown fungi at the infected area/site, providing symptomatic relief to a subject in need thereof, successfully eliminating the infection, curing the fungal infection, preventing recurrence of fungal infection, curing drug resistant fungal infections, and treatment of fungal infections in clinical non-responders and patients with barrier defects.

In some embodiments, the composition is administered to the subject in a therapeutically effective amount. By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250, 500, and 1,000 mg of the active ingredient for the symptomatic adjustment of the dosage to the subject to be treated. An effective amount of the drug is ordinarily supplied at a dosage level from 0.0002 mg/kg to about 20 mg/kg of body weight per day, especially from about 0.001 mg/kg to 7 mg/kg of body weight per day. In some embodiments, the composition is administered daily or 2, 3, 4, 5, 6, 7, or more times weekly.

Embodiments of the disclosure also include methods of preparing the ligand and complexes as described herein. Such methods may utilize conventional organic chemistry techniques, e.g. as described in the Example herein. For example, embodiments provide a method for synthesizing a ligand having the formula (E)-4-bromo-2-{[(2,3-dihydrobenzo[b][1,4]dioxin-6-yl)imino]methyl}phenol, comprising reacting 2,3-dihydrobenzo[b][1,4]dioxin-6-amine with 5-bromo-2-hydroxybenzaldehyde under conditions suitable for forming the ligand.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order, which is logically possible.

EXAMPLE

Methods

As shown in FIG. 1, we first synthesized the ligand having the formula (E)-4-bromo-2-{[(2,3-dihydrobenzo[b][1,4]dioxin-6-yl)imino]methyl}phenol (L). The ligand was subsequently used for the synthesis of the homoleptic metal complexes. An ethanolic solution of 2,3-dihydrobenzo[b][1,4]dioxin-6-amine (0.15 g, 1 mmol) was added dropwise to an ethanolic solution of 5-bromo-2-hydroxybenzaldehyde (0.20 g, 1 mmol) with constant stirring for an hour. A bright yellow precipitate was obtained, filtered and dried in a desiccator over anhydrous $CaCl_2$. The Yield was achieved as: 75%. m.p.: 119° C. Anal. calc. for $C_{15}H_{12}BrNO_3$ (333.00 gmol$^{-1}$): C, 53.91; H, 3.62; N, 4.19. Found: C, 53.89; H, 3.66; N, 4.17. FT-IR (KBr) cm$^{-1}$: $\nu$(OH) 3586, $\nu$(C=N) 1607, $\nu$(C=Cring) 1493, $\nu$(C—O) 1278. $^1$HNMR (400 MHz, DMSO-$d_6$, 25° C., δ ppm): 13.19 (m, 1H; OH), 8.88 (s, 1H; CH=N), 6.91-7.81 (6H; Ar), 4.27 (s, 4H; $CH_2$). $^{13}$CNMR (100 MHz, DMSO-$d_6$, 25° C., δ ppm): 160 (—C=N— imine), 144.30, 141.51, 138.93, 135.54, 134.36, 130.92, 121.66, 119.42, 118.05, 115.72, 110.05, 107.63, 102.07 (Ar—C), 64.61. Mass spectrum (ESI) [M+H]$^+$=334.00 (Br$^{79}$), 336.00 (Br$^{81}$); UV-Vis (in DMSO); $\lambda_{max}$, nm; 254, 345.

Complex C1 was then prepared by the following method: 1 mmol of $[Co(OAc)_2] \cdot 4H_2O$ was added to a 2 mmol solution of ligand (L) in the appropriate solvent mixture (methanol and dichloromethane; 1:1) and the resulting clear solution was stirred for an hour at room temperature. After that, the solution was left exposed to air and crystallization took place by slow evaporation for complex C1. The obtained complex was washed with methanol, diethylether and finally dried in a desiccator over anhydrous $CaCl_2$). $[Co(L)_2]$ (C1). The yield is given as: 65%. m.p.: 195° C. Molar conductance (10$^{-3}$ M, MeOH): 13 Ω$^{-1}$ cm$^{-2}$ mol$^{-1}$. Anal. calc. for $C_{30}H_{22}Br_2CoN_2O_6$ (722.24 g mol$^{-1}$): C, 49.68; H, 3.06; N, 3.86. Found: C, 49.63; H, 3.11; N, 3.85%. IR (KBr) cm$^{-1}$: $\nu$(C=N) 1576, $\nu$(C—H) 2925, $\nu$(C=Cring) 1441, $\nu$(C—O) 1143, $\nu$(NN) 1140, $\nu$(Co-0) 523, $\nu$(Co—N) 422. Mass spectrum (ESI) [M+2H]$^+$=724.24. UV-vis (in DMSO); $\lambda_{max}$, nm; 254, 327 457, 553.

Complex C2 [Ni(L)$_2$(H$_2$O)$_2$] (C2) was also prepared. Complex C2 was synthesized by a procedure similar to the C1 with only Ni(OAc)$_2 \cdot 4H_2O$ being used in place of Co(OAc)$_2$)·4H$_2$O. The reaction resulted in the formation of orange coloured precipitate which was collected after several washings with methanol and diethyl ether and dried in a desiccator over CaCl$_2$). Yield: 63%. m.p.: 227° C. Molar conductance (10$^{-3}$ M, MeOH): 19 Ω$^{-1}$ cm$^{-2}$ mol$^{-1}$. Anal. calc. for $C_{30}H_{26}Br_2N_2NiO_8$ (757.94 g mol$^{-1}$): C, 47.35; H, 3.44; N, 3.68. Found: C, 47.38; H, 3.34; N, 3.93%. IR (KBr) cm$^{-1}$: $\nu$(OH) 3426, $\nu$(C=N) 1575, $\nu$(C—H) 2925, $\nu$(C—O) 1143, $\nu$(M-O) 517, $\nu$(M-N) 452. Mass spectrum (ESI) [M+H]$^+$=758.93. UV-vis (in DMSO); $\lambda_{max}$, nm; 275, 373, 523, 635, 708.

Complex C3[Cu(L)$_2$] (C3) was also prepared. A similar procedure like that for C1 was involved in the synthesis of C3 with only Cu(OAc)$_2 \cdot H_2O$ being used in place of Co(OAc)$_2$)·4H$_2$O. The reaction resulted in the formation of brownish precipitate which was collected after several washings with methanol and diethyl ether and dried in a desiccator over CaCl$_2$. Yield: 63%. m.p.: 222° C. Molar conductance (10$^{-3}$ M, MeOH): 15 Ω$^{-1}$ cm$^{-2}$ mol$^{-1}$. Anal. calc. for $C_{30}H_{22}Br_2CuN_2O_6$ (726.91 g mol$^{-1}$): C, 49.37; H, 3.04; N, 3.84. Found: C, 49.42; H, 3.14; N, 3.78%. IR (KBr) cm$^{-1}$: $\nu$(C=N) 1583, $\nu$(C—H) 2927, $\nu$(C—O) 1305, $\nu$(M-O) 515, $\nu$(M-N) 447. Mass spectrum (ESI) [M]$^+$=726.91. UV-vis (in DMSO); $\lambda_{max}$, nm; 262, 361, 460, 695.

Complex C4 [Zn(L)$_2$(H$_2$O)$_2$] (C4) was also prepared. Complex C4 was prepared using a similar procedure like that for C1 but using Zn(OAc)$_2 \cdot 4H_2O$ in place of Co (oAc)$_2$)·4H$_2$O. Yellow precipitate obtained was washed with methanol and diethyl ether and dried in a desiccator over CaCl$_2$). Yield: 63%. m.p.: 219° C. Molar conductance (10$^{-3}$ M, MeOH): 12 Ω$^{-1}$ cm$^2$ mol$^{-1}$. Anal. calc. for $C_{30}H_{26}Br_2N_2O_8Zn$ (763.93 g mol$^{-1}$): C, 46.93; H, 3.41; N, 3.65. Found: C, 47.03; H, 3.43; N, 3.71%. IR (KBr) cm$^{-1}$: $\nu$(OH) 3432, $\nu$(C=N) 1575, $\nu$(C—H) 2873, $\nu$(C—O) 1149, $\nu$(M-O) 469, $\nu$(M-N) 405. Mass spectrum (ESI) [M+H]$^+$= 764.94. UV-vis (in DMSO); $\lambda_{max}$, nm; 251, 338, 428.

In this work, nine strains of *C. albicans* procured from Charlotte Maxeke Johannesburg Academic Hospital under ethical clearance number M000402 were employed (Table 1). All the *C. albicans* strains were preserved at −70° C. deep freezer in 50% (v/v) anhydrous glycerol (Sigma-Aldrich St. Louis, MO, U.S.A.). For conducting experiments, cultures were revived in Sabouraud Dextrose broth (SDB; Merck, Germany) at 37° C. and 120 rpm for 24 h. Additionally, the RPMI 1640 medium and MOPS (Sigma-Aldrich, USA) were prepared as described by the Clinical and Laboratory Standards Institute (CLSI).

TABLE 1

| Fungal isolates | |
|---|---|
| Control | 1. *C. albicans* SC5314 |
| Flz sensitive | 2. *C. albicans* 4554 |
| | 3. *C. albicans* 4251 |
| | 4. *C. albicans* 4175 |
| | 5. *C. albicans* 4180 |
| Flz resistant | 6. *C. albicans* 4324 |
| | 7. *C. albicans* 4106 |
| | 8. *C. albicans* 5112 |
| | 9. *C. albicans* 4085 |

The activity of C1 against *Candida* species (n=9) was first estimated in terms of minimum inhibitory concentration (MIC) and minimum fungicidal concentration (MFC). The MIC values were evaluated by the microdilution method suggested in the CLSI guidelines [CLSI M27-A4]. Briefly, stock solutions of Flz (used as reference; Sigma-Aldrich St. Louis, MO, U.S.A.) and the synthesized compound was prepared in 1% dimethyl sulfoxide (DMSO; Sigma-Aldrich St. Louis, MO, U.S.A.) and the test concentrations were formulated in RPMI 1640-MOPS medium. A two-fold dilution of the compound (1250-0.61 µg/mL) and reference drug (128-0.062 µg/mL) was prepared in 96 well plates which were then seeded with *C. albicans* inoculum ($1 \times 10^6$ cells/mL) and incubated at 37° C. for 24 h. In every set of experiments, sterility control, 1% DMSO as negative control and growth control were included. Growth was quantified by reading the optical density at 620 nm in a UV-1800 SHIMADZU spectrophotometer (Shimadzu Corporation, Japan). The MIC was determined as the lowest concentration that inhibited the growth of *Candida* strains. To determine MFC, each well without visible growth was subcultured onto the SDA plates for 24 hours at 37° C. The lowest concentration killing ≥99.9% of *Candida* was taken as the MFC value of the test compound.

Quantification of Live/Dead *C. albicans* cells in response to C1 was carried out. The actual count of viable and dead cells of *C. albicans* by treatment of C1 was monitored by Cell Count and Viability assay kit. An inoculum ($1 \times 10^6$ cells/mL) of both Flz sensitive (*C. albicans* 4251) and resistant (*C. albicans* 5112) *C. albicans* strains was prepared followed by treatment with various concentrations of C1 (0.5×MIC, 1×MIC and MFC) for 24 h at 37° C. and 150 rpm. For the negative control, only inoculum treated with 1% DMSO was used and for the positive control, hydrogen peroxide (10 mM) was used in a 1:1 ratio with the inoculum. Following incubation, the cells were then washed in PBS and centrifuged at 4000 rpm for 5 minutes at 4° C. and the final pellet was resuspended in PBS. The Cell Count and Viability assay samples were prepared by mixing 190 µL of Luminex Cell Viability Dilution Buffer and 10 µL of the sample in a 1.5 mL Eppendorf tube and incubated in the dark for 5 min at room temperature. All samples were analysed by a Guava® Muse® Cell Analyser (Luminex A DiaSorin Company, USA).

To examine the effect of C1 on the induction of cellular apoptosis in *C. albicans* cells, crucial apoptotic markers were observed. For this purpose, *C. albicans* 4251 and *C. albicans* 5112 cells were subjected to protoplast preparation by utilizing a method described previously by Srivastava et al. in 2020 through their research study. Briefly, cells were grown overnight and were exposed for 4 h with different concentrations of C1 (0.5×MIC and 1×MIC) and $H_2O_2$ (positive control) whereas, untreated cells were used as a negative control. Later on, the cells were washed and incubated for 10 min at room temperature in protoplast buffer-1 (1M sorbitol, 0.05M tris base, 0.01M $MgCl_2$, 0.03M DTT, pH 7.4). The cells were spun at 1500 rpm for 5 min and the pellet was resuspended in protoplast buffer-2 (1M sorbitol, 0.05M tris base, 0.01M $MgCl_2$, 0.001M DTT, pH 7.4) supplemented with lyticase enzyme (1 µg/mL) and incubated for 1 h at room temperature. Afterwards, the cell suspension was again centrifuged, and the pellet was resuspended and incubated for 20 min at room temperature in protoplast buffer-3 (1M sorbitol, 0.05M tris base, 0.01M $MgCl_2$, pH 7.4). A final washing (1500 rpm for 5 min) was given to the cells and the pellet consisting of *C. albicans* protoplasts was resuspended in fresh PBS and was stored at 4° C. until further use.

Measurement of mitochondrial membrane potential in *C. albicans* was carried out and the potential of C1 in destabilising mitochondrial membrane potential ($\Delta\psi m$) in *C. albicans* was established by JC-10 mitochondrial membrane potential assay kit (Abcam, Cambridge, UK). The experiment was performed according to manufacturer instructions. 90 µL of prepared protoplast of *C. albicans* 4251 and *C. albicans* 5112 was added to a 96-well microplate (with black walls and clear bottom), followed by the addition of 50 µL/well of JC-10 dye-loading solution. The microplate was incubated for 1 hour at 37° C. in the dark. This was followed by the addition of 50 µL/well of assay buffer B. The microplate was then immediately centrifuged at 800 rpm for 2 minutes. The fluorescence intensity was monitored at an Ex/Em=490/530 nm (present in apoptotic cells, monomeric form and green fluorescence; represented as X) and 540/590 nm (present in live cells, dye aggregates and red fluorescence; represented as Y) using a SpectraMax® ID3 Multimode Plate Reader (Molecular Devices, LLC., USA). The ratio between the aggregate and monomeric forms was measured to find the change in mitochondrial membrane potential. The mitochondrial membrane depolarization is indicated by decreasing ratio values.

The role of C1 in the modulating cytochrome c oxidase activity in *C. albicans* was investigated. The mitochondria from *C. albicans* 4251 and *C. albicans* 5112 were isolated using Yeast Mitochondria Isolation Kit—MITOISO3 (Sigma-Aldrich St. Louis, MO, U.S.A.) and then the Cytochrome c oxidase assay kit (ScienCell, Cat. No. 8278, CA, USA) was used to detect the cytochrome c oxidase activity in the cells following the manufacturer's instructions. Briefly, the *C. albicans* protoplasts were homogenized and the homogenate was resuspended and centrifuged in storage buffer (1×, 1 mL) at 6,500×g at 4° C. (10 min). The supernatant was discarded and resuspended in 200 µL of storage buffer (1×). The TCA Lowry method was utilized for determining the protein concentration present in the sample. Later on, the estimation of cytochrome c oxidase activity was done by preparing an assay mixture (Assay Buffer, 940 µL; n-dodecyl β-D-maltoside solution, 10 µL; mitochondrial protein, 2 µg) in a cuvette and then adding cytochrome c substrate solution (50 µL, provided in the kit) to it. Any change in absorbance was measured on a kinetic program (550 nm; every 30 seconds with an interval of 5 seconds) by using a spectrophotometer (UV-1800, Shimadzu Corporation, Japan).

We further performed an assay to detect the presence of DNA damage in *C. albicans*, an indicator of late-stage apoptosis. For this purpose, we used Click-iT Plus TUNEL® assay kit (Thermo Fisher Scientific, MA, USA) and the experiment was conducted as suggested by the manufacturer. Following protoplast preparation, each sample (15 µL) was spotted onto a glass slide and was allowed to dry at room temperature. Later on, the cells were fixed using glutaraldehyde (4%) at room temperature. Fixed cells were then washed and permeabilized with Triton X-100 (0.25%) for 30 min at room temperature followed by washing twice with PBS. To each sample the TdT Reaction Buffer (50 µL) was added and incubated (10 min) at room temperature. Following incubation, the reaction buffer was decanted and TdT Reaction Mixture (50 µL) was added to each sample. The slides were then incubated for 60 minutes in a humidified chamber followed by washing twice with Bovine Serum Albumin (3%; BSA). After washing, Click-iT Plus TUNEL® Reaction cocktail (50 µL) was instantaneously added to each sample and kept for 30 minutes in a dark room. The reaction cocktail was then decanted, and slides were washed with BSA (3%). To achieve DNA staining, 100 µL of Hoechst 33342 dye (1×; Thermo Fisher Scientific, MA, USA) was added to each sample and incubated for 15 minutes at room temperature while being protected from light. The protoplasts were again washed with PBS and all the samples were examined under a fluorescence microscope using Zeiss Laser Scanning Confocal Microscope (LSM) 780 (Carl Zeiss Microscopy, Jena, Germany). An Ex/Em=495/519 nm was used for analysing the samples. For the Hoechst 33342 dye, an Ex/Em=350/460 nm was used.

The effect of C1 on the cell cycle of *C. albicans* 4251 and *C. albicans* 5112 was determined using Cell Cycle kit MCH100106 in a Guava® Muse® Cell Analyser according to the manufacturer's instructions. The cells of the *C. albicans* ($1 \times 10^6$ cells/mL) were exposed to C1 for 4 h at different concentrations (0.5×MIC and 1×MIC). Each sample was rinsed with fresh PBS after exposure, and the pellet was fixed in 1 mL of 70% ice-cold ethanol (Sigma Aldrich Co., USA). The Cell Cycle assay was prepared by mixing the 100 μL of Luminex® Cell Cycle dye and 100 μL of the prewashed fixed cells and incubated in the dark for 30 minutes at room temperature. All samples were analysed by a Guava® Muse® Cell Analyser (Luminex® A DiaSorin Company, USA). During the experiment, both the negative (without treatment) and positive control (10 mM $H_2O_2$ treated) were used.

To determine the cytotoxicity of C1, horse red blood cells (H-RBC; NHLS, Johannesburg, South Africa) were used. The horse blood was centrifuged, and the cell pellet was secured and washed three times with cold PBS. The final pellet was dissolved in cold PBS to make a 10% H-RBC solution. From this solution, 15 mL of 1% H-RBC solution was again prepared with the help of PBS. Then, 1 mL was aliquoted and added to various concentrations (0.5×MIC, 1×MIC, 2×MIC and 4×MIC) of C1 in 2 mL Eppendorf tubes. The negative control consisted of the RBC solution mixed with PBS; while the positive control consisted of RBC mixed with 1% Triton X-100. The samples were incubated for 4 h at 37° C. Following incubation, the samples were centrifuged at 2000 rpm for 10 minutes and supernatant (200 μL) was transferred to a flat-bottomed 96-well microtiter plate and the absorbance was measured at 450 nm using a SpectraMax ID3 Multimode Plate Reader (Molecular Devices, LLC., USA). The percentage of haemolysis was calculated by using the following equation:

$$\% \text{ Haemolysis} = \left[ \frac{A450 \text{ of test compound treated sample} - A450 \text{ of buffer treated sample}}{A450 \text{ of 1\% Triton X} - 100 \text{ treated sample} - A450 \text{ of buffer treated sample}} \right] \times 100\%$$

Statistical analysis for all the experiments were performed in triplicate and final outcomes were analysed by GraphPad Prism® using two-way ANOVA test. Statistical significance was calculated in terms of p value (*p<0.001, p<0.01 and *p<0.1).

Results

Characterization of the Ligand (L) and its Metal Complexes (C1-C4)

As shown in FIG. 1, the reaction of two equivalents of ligand (L) dissolved in methanol/DCM (1:1) with one equivalent of $[Co(OAc)_2]\cdot 4H_2O$, $[Ni(OAc)_2]\cdot 4H_2O$, $[Cu(OAc)_2]\cdot H_2O$ and $[Zn(OAc)_2]\cdot 2H_2O$ in alcoholic solvent (ROH; R=$CH_3$, $C_2H_5$) under ambient conditions, resulted in the successful synthesis of Co(II), Ni(II), Cu(II) and Zn(II) complexes, $[Co(II)(L)_2]$ (C1), $[Ni(II)(L)_2(H_2O)_2]$ (C2), $[Cu(II)(L)_2]$(C3), and $[Zn(II)(L)_2(H_2O)_2]$ (C4) in which the metal coordinated acetate molecules are replaced by the ligand moieties. Here, the ligand behaves as NO bidentate coordinating through its iminic-N and phenolate-O atoms. The synthesized complexes are air stable and soluble in most common organic solvents.

Spectroscopic studies revealed that the ligand (L) adopted an enol tautomeric form, and on complexation, deprotonation of the ligands resulted in the formation of the complexes C1, C2, C3 and C4, respectively (FIG. 1). The different physico-chemical properties of Schiff base ligand (L) and its metal complexes (C1-C4) are given in Table 2. The molar conductivities of the complexes (C1, C2, C3 and C4) are in the range of 12-19 $\Omega^{-1}cm^{-2}$ $mol^{-1}$ which agrees with their non-electrolytic behaviour. Furthermore, infrared spectra, UV-Visible and other spectroscopy and physical techniques completely agreed with the composition of the synthesized compounds.

TABLE 2

Physicochemical properties of Schiff base ligand (L) and its complexes (C1-C4)

| Compound | Color | Mol. formula | Mol. Wt. | Yield (%) | $\Lambda_m$ ($\Omega^{-1}cm^2mol^{-1}$) | Mp (° C.) | $\mu_{eff}$ (BM) |
|---|---|---|---|---|---|---|---|
| L1 | Bright Yellow | $C_{15}H_{12}BrNO_3$ | 333.00 | 75 | — | 119 | — |
| C1 | Brown | $[C_{30}H_{22}Br_2CoN_2O_6]$ | 722.24 | 63 | 13 | 195 | 4.22 |
| C2 | Orange | $[C_{30}H_{26}Br_2N_2NiO_8]$ | 757.93 | 58 | 19 | 227 | 3.31 |
| C3 | Brown | $[C_{30}H_{22}Br_2CuN_2O_6]$ | 726.91 | 69 | 15 | 222 | 1.74 |
| C4 | Yellow | $[C_{30}H_{26}Br_2N_2O_8Zn]$ | 763.93 | 72 | 12 | 219 | Diamag. |

The infrared spectrum of the ligand (L) displayed absorption bands at 3586 and 1607 $cm^{-1}$ ascribed to the —OH and —HC=N-stretching vibrations, respectively. The clearly evident shifts and disappearance of the peaks upon complexation (for C1, C2, C3 and C4) confirms the coordination via the deprotonated phenolic oxygen and the iminic nitrogen to the metal ions. In the complexes, the band due to azomethinic group shifted to lower wave numbers by 31, 32, 24 and 31 $cm^{-1}$ for C1, C2, C3 and C4 respectively, suggesting the coordination of the azomethine nitrogen to the cobalt, nickel, copper and zinc ions in the complexes.

The appearance of new peaks in the range of 531-423 $cm^1$ may be assigned M=O and M=N (M=Co, Ni, Cu and Zn) vibrations in the complexes. The $^1$H-NMR spectrum of the ligand (L) showed a singlet at 13.19 ppm and 8.88 ppm for the —OH and —CH=N-proton resonances, respectively. In the ligand (L), a sharp singlet at 4.27 ppm was assigned to the $CH_2$ protons and the aromatic protons lie between 6.1 and 7.81 ppm as multiplets. In the $^{13}$C-NMR spectrum of the ligand (L) the phenolic carbon appeared at 159 ppm and the chemical shifts of carbon atoms of phenyl rings were found in the region 102-144 ppm while as the carbon of azomethinic (—CH=N—) group appears at 160 ppm. The UV-Vis absorption spectra of the complexes C1, C2, C3 and C4 as well as the free organic ligand (L), were studied in the 200 nm to 800 nm wavelength range.

The Schiff base ligand (L) shows an intense absorption band at 254 nm region, corresponding to a π-π* transition of the phenyl group and another absorption band at about 345 nm arises from the phenol-imine form, which may be attributed to n-π* type transitions, respectively. The coordination of the ligand (L) with cobalt, nickel, copper and zinc gives a clear blue shift of the π-π* transition bands. In complex C1 the absorption band in the visible region at 553 nm has been ascribed to a $^4A_2(F) \rightarrow {}^4T_1(F)$ transition suggesting its tetrahedral nature and in complex C3 the expected transitions, $^2B_{1g} \rightarrow {}^2A_{1g}$ and $^2B_{1g} \rightarrow {}^2E_g$ supported a square planar geometry for the complex. Furthermore, the geometries were supported by the observed magnetic moments which were 4.22 BM for C1 complex and 1.74 BM for C3 complex respectively. The absorption spectrum of C2 displayed three absorption bands at 523, 635 and 708 nm which may be attributed to $^3A_{2g} \rightarrow {}^3T_{1g}(P)$, $^3A_{2g} \rightarrow {}^3T_{1g}(F)$ and $^3A_{2g} \rightarrow {}^3T_{2g}$ transitions respectively. In addition, a band at 398 nm has been assigned to ligand to metal charge transfer. The observed magnetic moment for the complex C2 was found to be 3.31 B.M confirming an octahedral geometry around the Ni(II) ion. In complex C4, the absorption band found at 428 nm may be attributed to the ligand to metal charge transfer with zero magnetic moment. Due to the diamagnetic nature of complex C4, no d-d bands were observed, and an octahedral geometry has been proposed for the complex C4. The shifts indicate that complexes C1, C2, C3 and C4 chelate with the ligands through imine-N and phenolate-O.

The mass spectra of the Schiff base ligand (L) and complexes (C1-C4) presented moderate to high relative intensity molecular ion peaks. It is obvious that the molecular ion peaks are in good agreement with the proposed empirical formula of the compounds. The mass spectra of Schiff base ligand (L) displayed molecular ion peak at m/z 334.00 $[M+H]^+$. The mass spectra of metal complexes (C1, C2, C3 and C4) showed molecular ion peaks at 724.24$[M+2H]^+$, 758.93$[M+H]^+$, 726.91$[M]^+$ and 764.94$[M+H]^+$, respectively.

Thermogravimetric analysis of the complexes C1, C2, C3 and C4 was obtained in the temperature range of 40-800° C. The thermograms of complexes C1 and C3 displayed a three-step decomposition while the thermograms of C2 and C4 complexes showed two step decompositions. In the TG curve of the C1 complex a weight loss in two steps with the first weight loss of 45% (calcd. 45.9%) in the region of 195-430° C. is related to the exothermic decomposition of one ligand molecule and the second weight loss of about 45% in the region of 430-700° C. (calcd. 45.9%) corresponds to the decomposition of another ligand molecule with CoO remaining as the residue. Complex C3 exhibited almost a similar decomposition pattern like that of complex C1, leaving CuO as the residue.

In complex C2, the first stage proceeded with a weight loss of 4.52% (calcd. 4.74%) in the temperature range of 100-200° C. This weight loss is due to the loss of two coordinated water molecules in the complex. The second stage in C2 continued with one degradation step with the weight loss of 43.07% (calcd. 43.74%) in the temperature range of 200-480° C. This weight loss is due to the loss of $C_{15}H_{11}BrNO_3$ fragment. The third stage occurred in the temperature range of 480-680° C. with the weight loss of 42% (calcd. 43.74%) due to the loss of $C_{15}H_{11}BrNO_3$ fragment. The overall weight loss observed in C2 was found to be 89.59% (calcd. 92.22%). The NiO left as the residue has the observed weight of 10.6% against the calculated value of 9.84%.

Complex C4 underwent degradation in three stages. The first degradation occurred at the temperature range of 100-185° C. with the weight loss of 4.32% (calcd. 4.71%) ascribed to two coordinated water molecules. The second stage of degradation occurred at the temperature range of 185-480° C. with the weight loss of 43.18% (calcd. 43.45%) which is due to the loss of $C_{15}H_{11}BrNO_3$ fragment. The third stage of degradation occurred in the temperature range of 480-685° C. with a weight loss of 42.92% (calcd. 43.45%) that is due to the loss of $C_{15}H_{11}BrNO_3$ fragment. The total weight loss was found to be 90.42% (calcd. 91.62%). The ZnO left as a residue has the observed weight of 10% against the calculated value of 10.65%. Considering the TG curve, it seems that all the synthesized complexes exhibit varying decomposition steps with slight variations in decomposition temperatures.

X-Ray Crystallography

Figure 2:
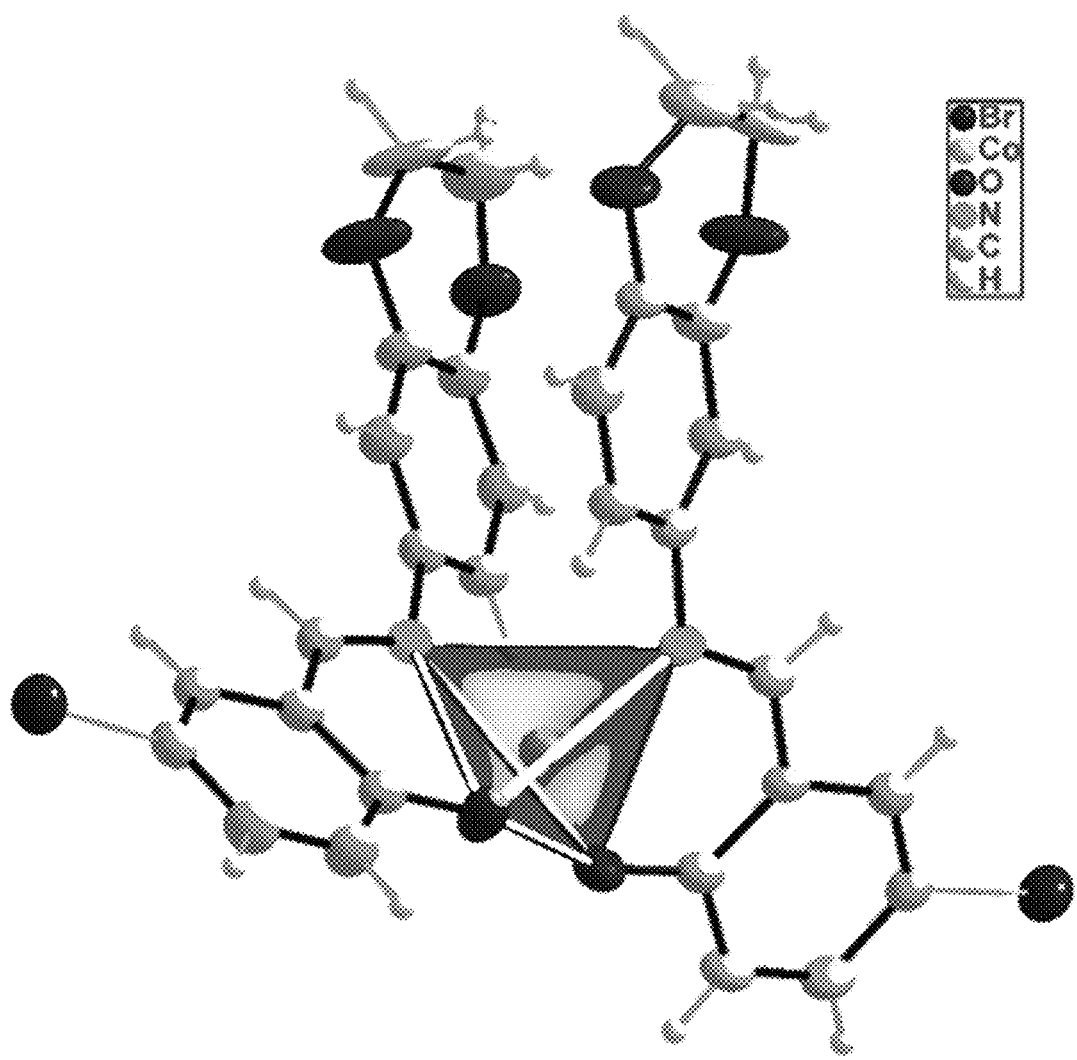
FIG. 2. Molecular structure of C1 displaying the polyhedron with ellipsoids drawn at the 50% probability level.
Figure 3:
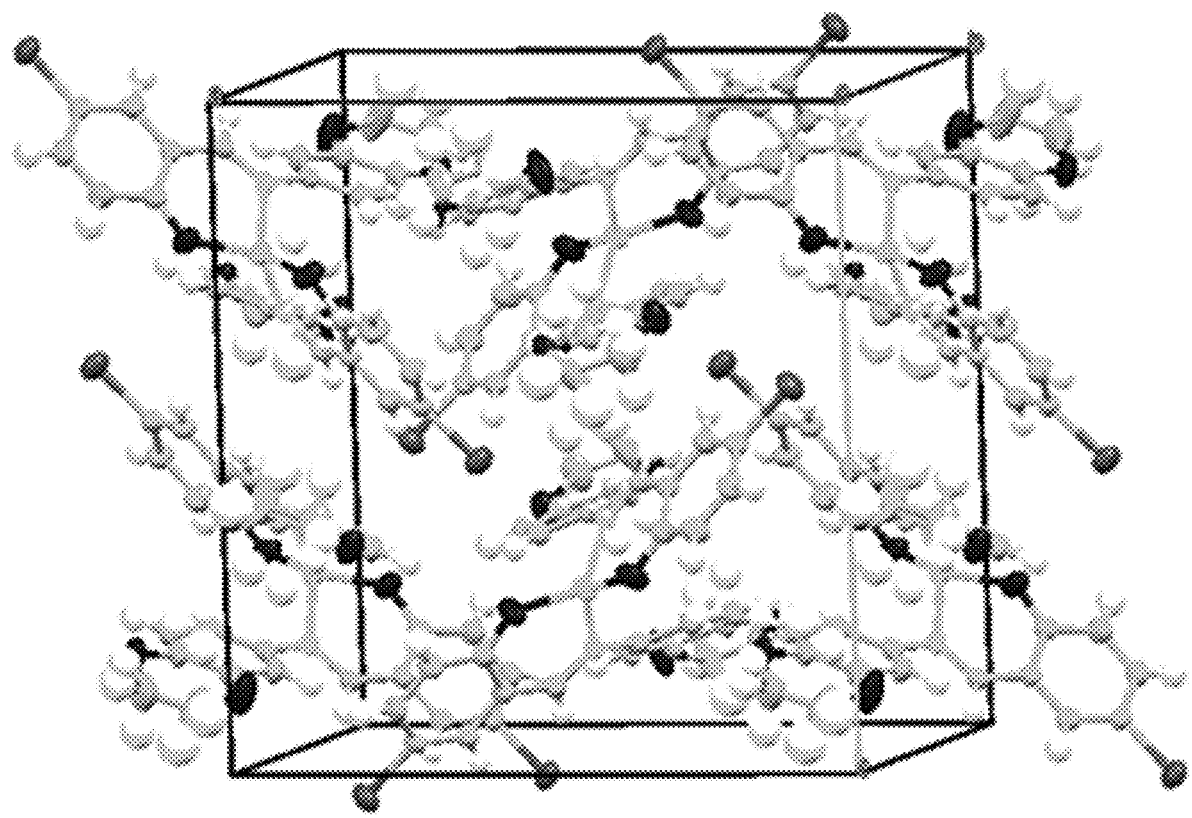
FIG. 3. Unit cell packing diagrams of the complex C1 displaying short contacts without hydrogen atoms.

Single crystals of a mononuclear cobalt complex suitable for X-ray diffraction were obtained after leaving the solution for slow evaporation at room temperature for several days. The ORTEP diagram and unit cell packing diagrams of the complex (C1) with different coloured atoms is shown in FIGS. 2 and 3.

The crystallographic study shows that C1 crystallizes in the orthorhombic system, Pcca space group; in which the central cobalt(II) lies at the center and is linked to nitrogen and oxygen donors of the two bidentate ligands (L) in a definite arrangement. The bond angles show that the coordination geometry of cobalt in C1 is distorted tetrahedral, with N004-Co02-O003, N004-Co02-O003 and O003-Co02-O003 angles of 127.22(11)°, 96.11(10)° and 109.97(16)°, respectively. The bond distances in the complex are 1.900 and 2.000 Å, for Co02-O003 and Co02-N004 bonds respectively, expected for a typical Schiff base ligand (containing a short —C═N—(N004-C00D) bond distance of 1.296 Å for C1) coordinated to a metal center, where the imine form is predominant. The observed Co02-O003 and Co02-N004 bonds in C1 are 1.900 and 2.000 Å, respectively (the normal bond lengths are 1.940 and 1.960 Å), so the coordination geometry around the Co(II) ion reflects the Jahn-Teller effect. The bidentate coordination inhibits forming intramolecular hydrogen bonds because of the deprotonated ligands, but there also exist two six-membered rings through a cobalt ion, two oxygens, and two nitrogens in C1.

In Vitro Anti-*Candida* Activity of C1

The results from the broth microdilution assays indicated that C1 was significantly effective at inhibiting fungal growth in both sensitive and resistant strains of *C. albicans*. The results also indicated that C1 was equally effective against all the investigated strains of *C. albicans*. The MIC value ranged from 1.22-4.88 μg/mL for Flz susceptible strains whereas, higher MIC values (9.76-19.53 μg/mL) were recorded for Flz resistant strains. Comparatively, *C. albicans* 5112 possessed the highest MIC (19.53 μg/mL) and MFC (78.12 μg/mL) values among all tested strains of *C. albicans*. Furthermore, we found that *C. albicans* 5112 had the highest tolerance against both C1 and Flz.

*C. albicans* is the most frequently isolated fungus from the skin and mucous infection and drug resistance in this species of *Candida* present an important therapeutic concern. Therefore, novel antifungal agents with a targeted mode of action against *C. albicans* are urgently required to ease the problem of drug resistance. Herein, we present a thorough analysis to investigate the potency of C1 to eradicate *C. albicans*. To understand the mechanism of action, investigation to measure the capability of C1 in triggering cellular apoptosis and arresting the cell cycle in Flz resistant and sensitive strains of *C. albicans*. Based on the MIC values *C. albicans* 4251 (Flz susceptible) and *C. albicans* 5112 (Flz resistant) were selected for detailed studies. The data and MIC and MFC values of C1 against *C. albicans* are given in Table 3.

TABLE 3

|  | Strains used | C1 (µg/mL) | | Flz (µg/mL) |
|---|---|---|---|---|
|  |  | Median MIC | Median MFC | Median MIC |
| Control | C. albicans SC5314 | 2.44 | 4.88 | 0.25 |
| Flz sensitive | C. albicans 4554 | 2.44 | 4.88 | 0.25 |
|  | C. albicans 4251 | 4.88 | 9.76 | 0.5 |
|  | C. albicans 4175 | 1.22 | 2.44 | 0.25 |
|  | C. albicans 4180 | 2.44 | 4.88 | 0.25 |
| Flz resistant | C. albicans 4324 | 9.76 | 19.53 | 32.0 |
|  | C. albicans 4106 | 9.76 | 19.53 | 32.0 |
|  | C. albicans 5112 | 19.53 | 78.12 | 64.0 |
|  | C. albicans 4085 | 9.76 | 19.53 | 16.0 |

Quantification of Live/Dead C. albicans Cells

Figure 4A:
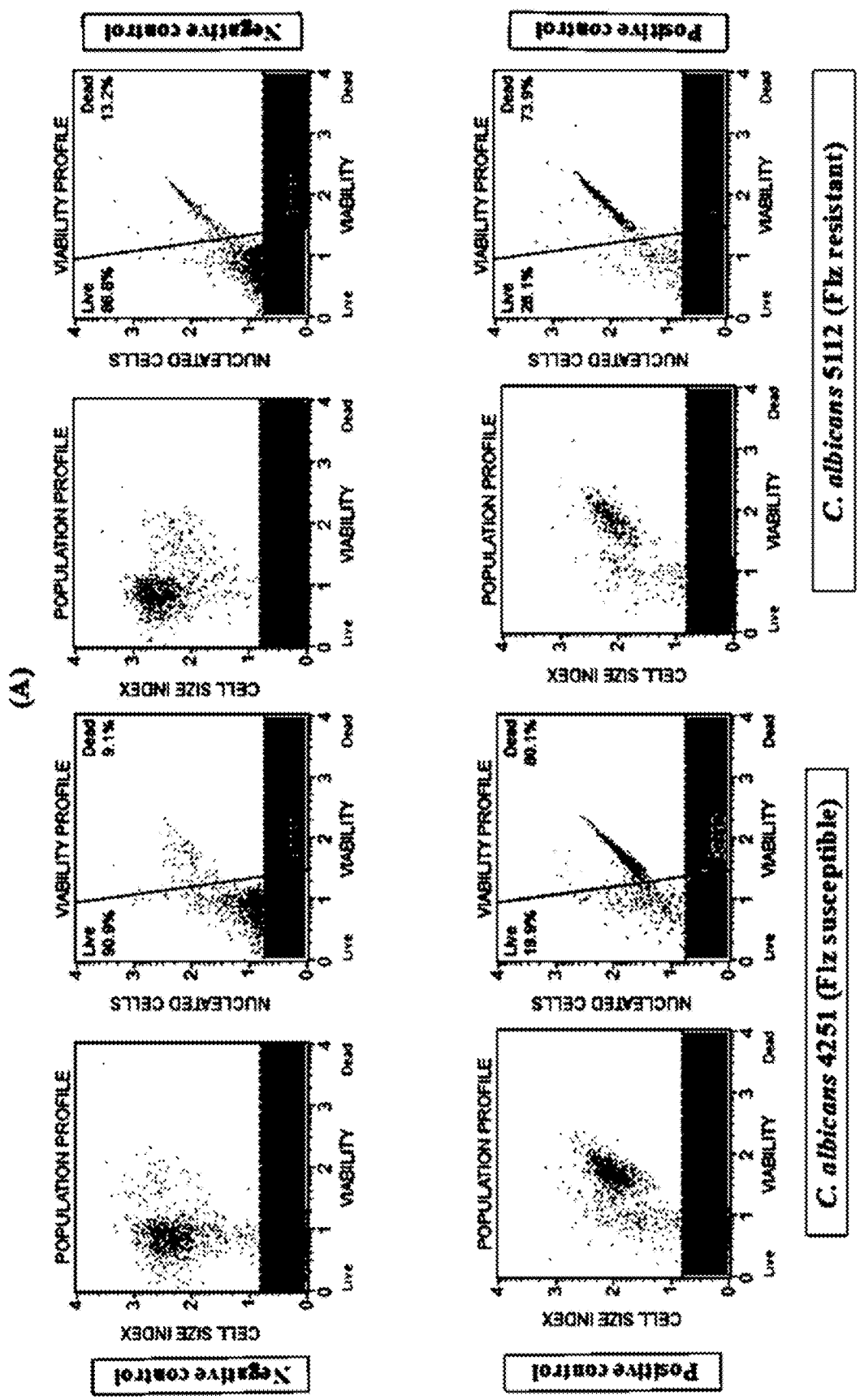
FIGS. 4A-B. Cell count and viability analysis measured by Muse® cell analyser. (A) Representation of the control experiment. (B) *C. albicans* 4251 (Flz susceptible) and *C. albicans* 5112 (Flz resistant) cells were treated with different concentrations of C1.
Figure 4B:
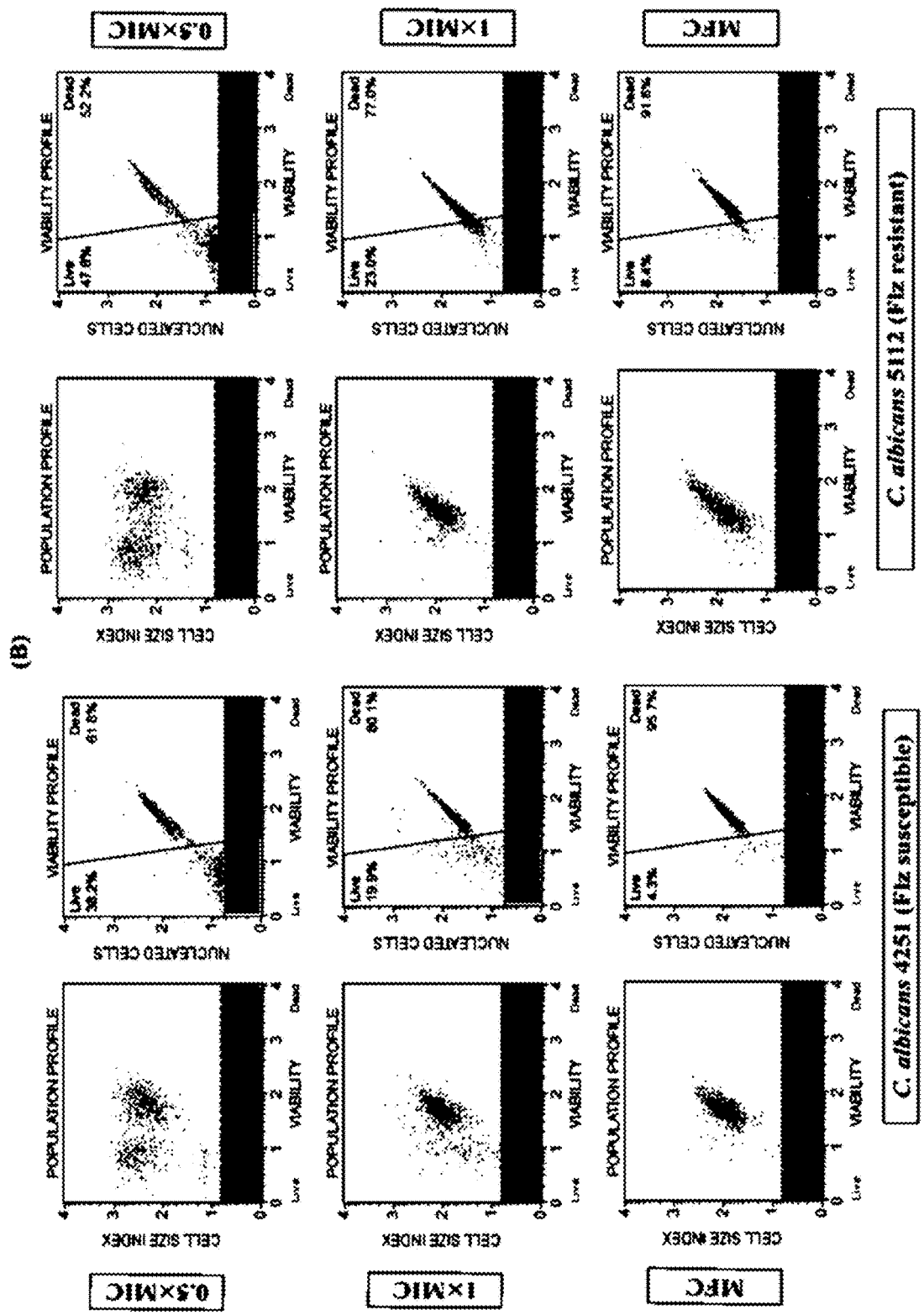

The results obtained from Muse® cell analyser were used to evaluate the anti-candida activity of C1. The cell count and viability profile of the C. albicans 4251 and C. albicans 5112 cells under different experimental conditions is shown in FIG. 4. The untreated negative control cells of C. albicans 4251 reported 90.9% live cells whereas, the positive control reported 19.9% live cells. Similarly, untreated cells of C. albicans 5112 reported 86.8% live cells and the positive control reported 26.1% live cells. The treated samples showed a relatively lower percentage of live cells with a rising concentration of C1. The maximum decrease was observed at the MFC value of C1 where 4.3% live cells and 8.4% live cells were recorded for Flz susceptible and resistant C. albicans strains respectively. These findings, therefore, supported our in vitro susceptibility assay and confirmed that C1 has strong candidicidal activity against both groups of C. albicans.

The results demonstrate that C1 is capable of killing both Flz susceptible and resistant C. albicans and this might be due to the induction of cellular apoptosis or necrosis. Therefore, we further validated our findings by studying some crucial apoptotic factors in strains of C. albicans and checked the effect of C1 on these parameters (mitochondrial membrane destabilization, cytochrome c oxidase activity and DNA damage).

The importance of mitochondria in supplying metabolic energy and playing a critical role in triggering cellular apoptosis has been well studied. Therefore, herein we also scrutinize the effect of C1 on mitochondrial membrane potential by using JC-10 fluorescent dye. During apoptosis, lowering of $\Delta\psi m$ is the key factor; the healthy cells are expected to possess stable $\Delta\psi m$ resulting in an aggregated form of JC-10 and thus a red fluorescence, whereas cells undergoing apoptosis lose their $\Delta\psi m$ and thus JC-10 remains monomeric giving a green fluorescence. To investigate the membrane destabilising effect of C1, $\Delta\psi m$ was quantified (JC-10 aggregates/JC-10 monomers) and lower values compared to untreated cells showed mitochondrial membrane depolarization ability of C1.

The results are represented in FIG. 5 displaying a decrease in the ratios after exposing C. albicans to C1 (0.5×MIC and 1×MIC). The results obtained in the positive control ($H_2O_2$ treated) were also found to deviate from the negative control (untreated cells). The average ratio calculated for negative and positive control was 2.92 and 2.75, respectively, for C. albicans 5112 cells. The average ratio for negative and positive control was 2.65 and 2.5 for C. albicans 4251. Whereas, upon exposure to 0.5×MIC of C1 the ratios decreased to 2.24 and 2.04 in C. albicans 5112 and C. albicans 4251 respectively. Furthermore, the ratio showed a sharp decline upon exposure to 1×MIC value, 1.71 and 1.6 for C. albicans 5112 and C. albicans 4251, respectively. Therefore, these observations clearly show that exposure to C1 results in destabilising membrane potential. The collapsing of the mitochondrial membrane has a direct impact on the activity of cytochrome c oxidase and finally causes apoptosis [Simon et al., 2000].

C1 decreased the activity of cytochrome c oxidase in C. albicans. The role of cytochrome c oxidase is to maintain a fine balance between cellular metabolism and apoptotic pathways. Therefore, it was important to investigate the effect of C1 on the activity of cytochrome c oxidase. Comparative analysis with negative control showed that upon exposure to C1, the cytochrome c oxidase activity was drastically lowered in both Flz resistant and sensitive strains of C. albicans in a dose-dependent manner (FIG. 6). The average percent decrease in the enzyme activity of Flz resistant strain was 14.2% and 47.53% at 0.5×MIC and 1×MIC values respectively. Whereas for Flz sensitive strain the average percent decrease in the enzyme activity was 22.61% and 51.3% at 0.5×MIC and 1×MIC values respectively. Therefore, C1 was found to be effective in depolarizing mitochondrial membrane potential, bleeding cytochrome c into cytosol and activating apoptotic factors in both Flz resistant and sensitive strains of C. albicans. This may trigger the caspase cascade-mediated apoptosis in C. albicans.

C1 resulted in DNA fragmentation in C. albicans. The terminal deoxynucleotidyl transferase-mediated dUTP nick end labelling (TUNEL) test is commonly used for studying DNA fragmentation in yeast cells, utilising this principal, we used this assay to understand whether C1 has an effect at the genetic level in C. albicans cells. The assay involved the insertion of modified dUTP at the 3'-OH ends of the broken DNA strand. A counterstaining with Hoechst 33342 dye (blue fluorescence) was done to differentiate normal yeast cells. The data obtained showed a concentration dependent effect on DNA fragmentation; with a rising concentration of C1, the TUNEL-positive cells (green, fluorescent spots) increased representing DNA fragmentation in the cell (FIG. 7). The cell population in negative control showed blue fluorescent spots. The results indicate that C1 is effective at inducing DNA fragmentation, a marker of late-stage apoptosis in yeast cells.

Cell Cycle Arrest in C. albicans Cells in Response to C1

Following exposure to C1 there was a considerable amount of DNA damage, which was confirmed by the TUNEL assay results. It is well known that cells which have experienced DNA damage are unable to enter and continue in the cell cycle. This prevents damaged cells from developing mutations that negatively impact the survival rate of future generations. For this reason, cell cycle arrest was studied. The cell population in the negative control was found well distributed among different phases of the cell cycle and this finding was common in both Flz resistant and sensitive strains of C. albicans. Although in $H_2O_2$ treated C. albicans the percentage of cells in different phases was almost similar to the negative control suggesting that there was not much impact of $H_2O_2$ on the cell cycle of C. albicans.

Figure 8A:
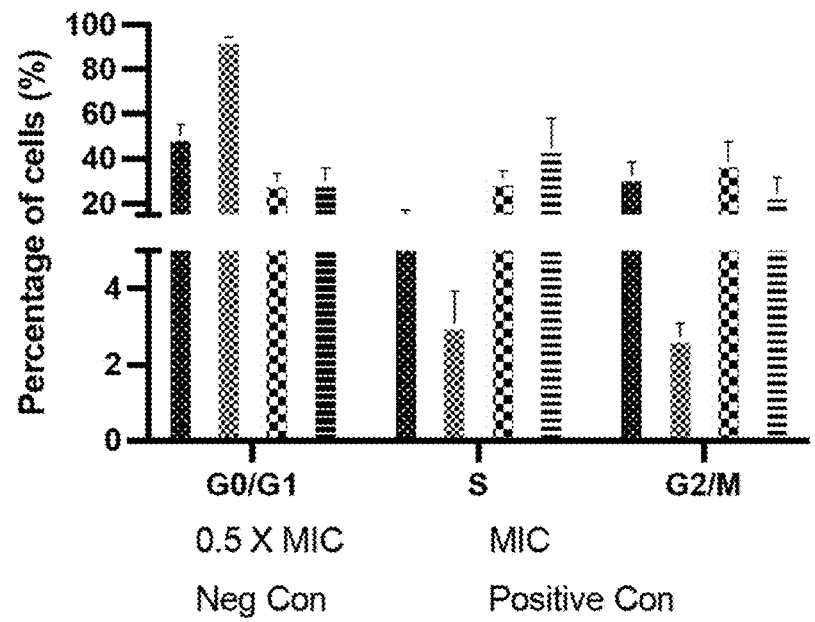
FIGS. 8A-B. Cell cycle analysis measured by Muse® cell analyser. (A) *C. albicans* 5112 (Flz resistant) cells and (B) *C. albicans* 4251 (Flz susceptible) and were treated with different concentrations (0.5×MIC and MIC) of C1.
Figure 8B:
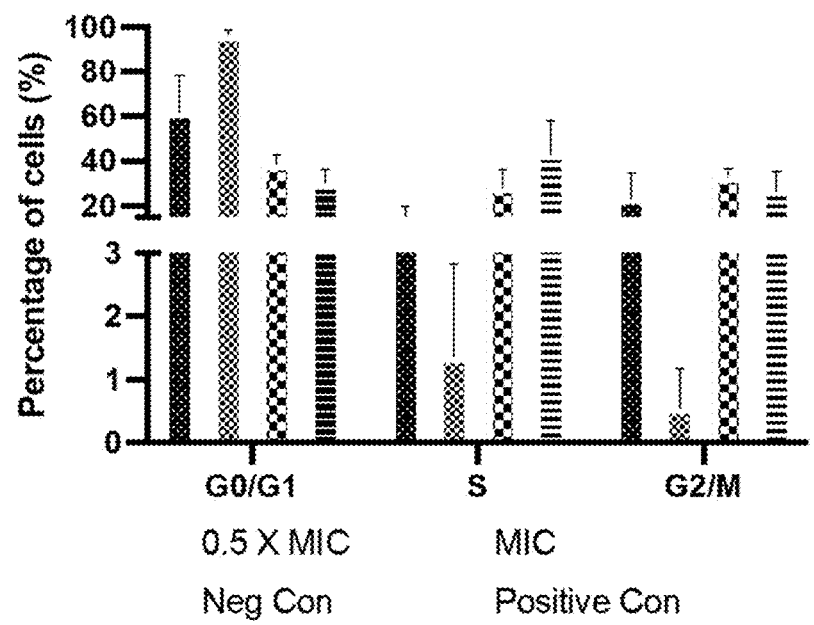

Contrary to these findings the exposure of C1 had a strong impact on the cell cycle physiology in both Flz resistant and sensitive strains of C. albicans (FIG. 8). It was observed that C1 at 0.5×MIC value C. albicans cells started aggregating in G0/G1 phase; an average of 50.8% (C. albicans 5112; Flz resistant) and 62% (C. albicans 4251; Flz sensitive) cells were restricted to G0/G1 phase of the cell cycle. Moreover, 1×MIC value caused cell cycle arrest in G0/G1 phase; an average of 94.1% and 96.55% cells were found sitting in the G0/G1 phase of the cell cycle in *C. albicans* 5112 and *C. albicans* 4251 respectively. The results clearly demonstrated the dose dependent impact of C1 on the *C. albicans* cell cycle.

Whenever a cell is exposed to any chemical agent having a cytotoxic effect, the DNA gets damaged and thus results in arresting cell division pathways which then leads to cell death. Moreover, the progression of the cell cycle is regulated by DNA damage checkpoints where any damage in DNA is detected, if possible then repaired and if not possible the cell undergoes apoptosis and the cell dies. Similarly, in yeast, the cell cycle is a key player of cellular growth and survival and if a chemical agent targets this critical cellular pathway, it can exert a strong antifungal activity.

Haemolytic Activity of C1

Figure 9:
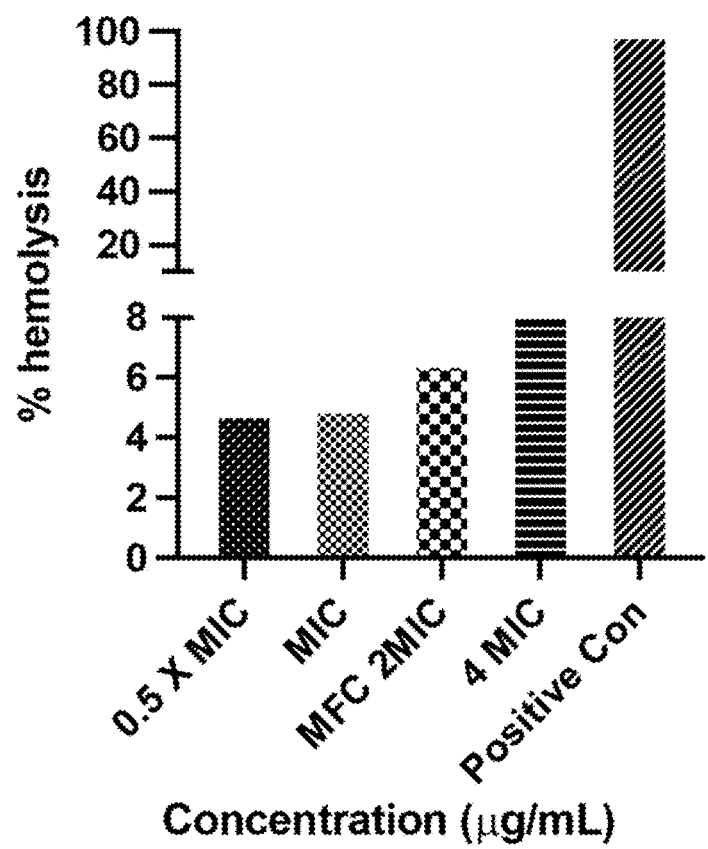
FIG. 9. Haemolytic activity of C1 at several concentrations (0.5×MIC–4×MIC). Positive control (RBC+1% Triton X-100) is used as a reference. PBS was used as a negative control.

The commonly used drugs against *Candida* species possess a high risk of toxicity and therefore, restrict their usage in critically ill patients. Henceforth, there is a pressing requirement to look for alternative options that result in targeted therapy without harming patients. Since, C1 presented significant activity against both Flz susceptible and Flz resistant *C. albicans* cells, therefore, toxicity determination of C1 was highly imperative. The results demonstrated that C1 produced haemolysis of the RBCs in the range of 5% to 10% (FIG. 9). The haemolytic activity was highest at 4×MIC values which were 10%. The aforementioned results established that C1 has considerably less haemolytic activity and thus should be safer for in vivo use.

While the invention has been described in terms of its several exemplary embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

ACKNOWLEDGMENT

The inventors extend their appreciation to the Deputyship of Research & Innovation, Ministry of Education in Saudi Arabia for funding this research work through the project number (IPPNC-011-130-2020) and King Abdulaziz University, DSR, Jeddah, Saudi Arabia.

What is claimed is:

1. A metal coordination complex, having the following formula:

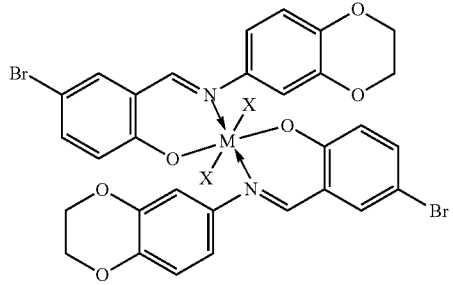

wherein
M is a transition metal; and
X is present or absent, and when present, is $H_2O$.

2. The metal coordination complex of claim 1, wherein M is cobalt.

3. The metal coordination complex of claim 1, wherein M is nickel.

4. The metal coordination complex of claim 1, wherein M is copper.

5. The metal coordination complex of claim 1, wherein M is zinc.

6. A pharmaceutical composition, comprising the metal coordination complex of claim 1 and a pharmaceutically acceptable carrier.

7. A method of inhibiting growth of a fungus, comprising contacting the fungus with an effective amount of the metal coordination complex of claim 1.

8. The method of claim 7, wherein the fungus is *Candida* spp.

9. The method of claim 8, wherein the fungus is *Candida albicans*.

10. The method of claim 7, wherein the fungus is resistant to azole antifungal agents.

11. The method of claim 10, wherein the azole is fluconazole.

12. A method for synthesizing a ligand having the formula (E)-4-bromo-2-{[(2,3-dihydrobenzo[b][1,4]dioxin-6-yl)imino]methyl}phenol, comprising reacting 2,3-dihydrobenzo[b][1,4]dioxin-6-amine with 5-bromo-2-hydroxybenzaldehyde under conditions suitable for forming the ligand.

* * * * *